United States Patent [19]
Webster, Jr.

[11] Patent Number: 6,090,104
[45] Date of Patent: *Jul. 18, 2000

[54] CATHETER WITH A SPIRALLY WOUND FLAT RIBBON ELECTRODE

[75] Inventor: Wilton W. Webster, Jr., Altadena, Calif.

[73] Assignee: Cordis Webster, Inc., Baldwin Park, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/486,522

[22] Filed: Jun. 7, 1995

[51] Int. Cl.[7] ...................................................... A61B 17/36
[52] U.S. Cl. ........................... 606/41; 607/116; 607/122; 600/374
[58] Field of Search ........................... 607/117–129, 116, 607/100–102, 99, 113; 606/41–50; 600/373–374

[56] References Cited

U.S. PATENT DOCUMENTS

| | | | |
|---|---|---|---|
| 4,481,953 | 11/1984 | Gold et al. ................................ | 607/122 |
| 5,133,365 | 7/1992 | Heil, Jr. et al. ........................... | 607/122 |
| 5,282,845 | 2/1994 | Bush et al. ................................ | 607/128 |
| 5,342,357 | 8/1994 | Nardella ................................. | 606/50 X |
| 5,383,923 | 1/1995 | Webster, Jr. ............................. | 607/125 |
| 5,582,609 | 12/1996 | Swanson et al. ..................... | 607/122 X |
| 5,603,697 | 2/1997 | Grundy et al. ....................... | 607/101 X |

*Primary Examiner*—Cary O'Connor
*Assistant Examiner*—Ryan Carter
*Attorney, Agent, or Firm*—Christie, Parker & Hale, LLP

[57] ABSTRACT

An electrode catheter comprising a tubular body with a distal section having a flexible tubular portion, wherein the flexible tubular distal section is covered by at least one spirally wrapped flat ribbon electrode. Each spirally wrapped flat ribbon electrode has an associated lead wire that can be connected to a source of energy for ablation or connected to a recording system to produce electrophysiologic signals for diagnosis. The preferred catheter is steerable by use of a puller wire connected to the distal section and connected to a handle with means for controlling the movement of the puller wire. In a preferred embodiment, the spirally wound flat ribbon electrode is partially masked with a polyurethane or latex mask.

13 Claims, 12 Drawing Sheets

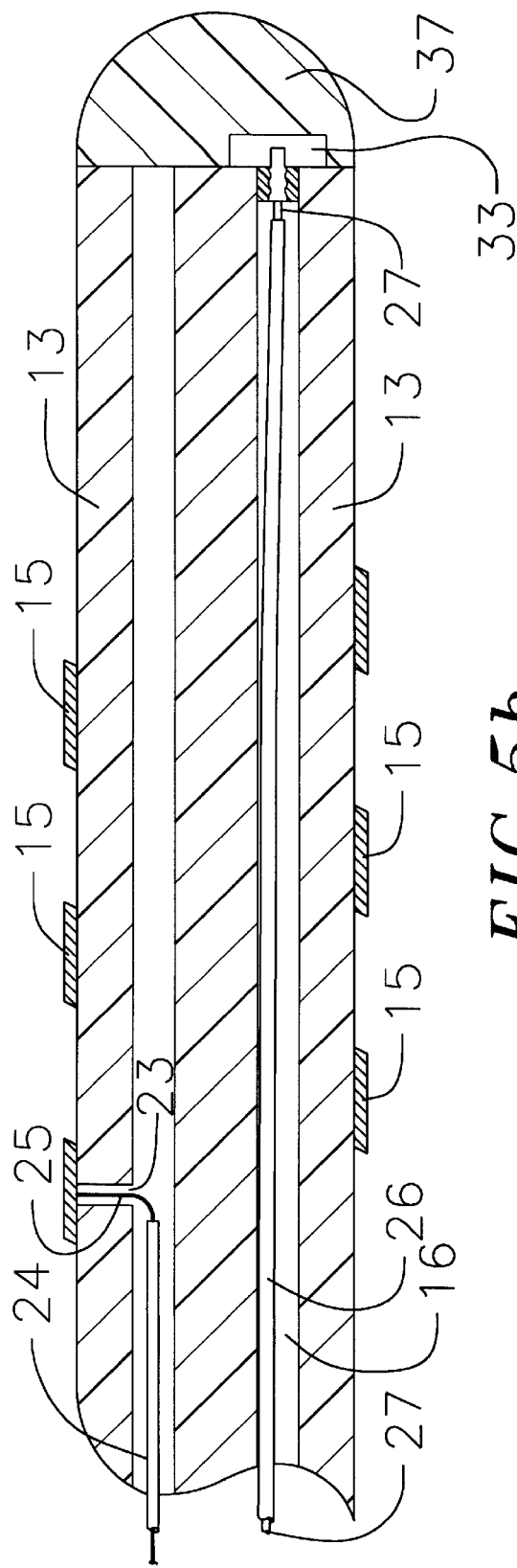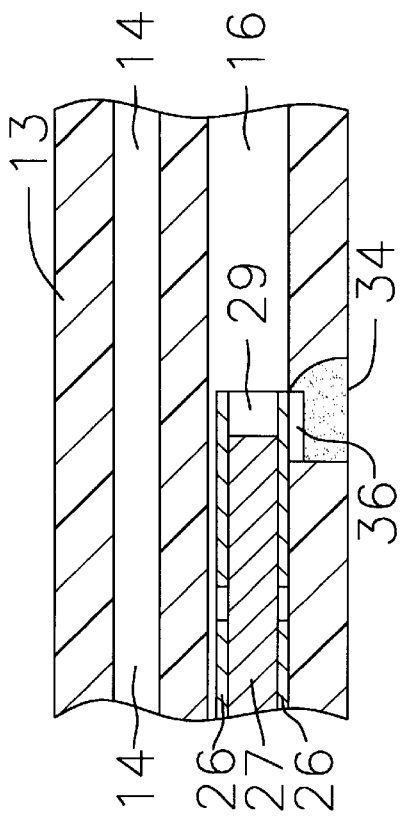

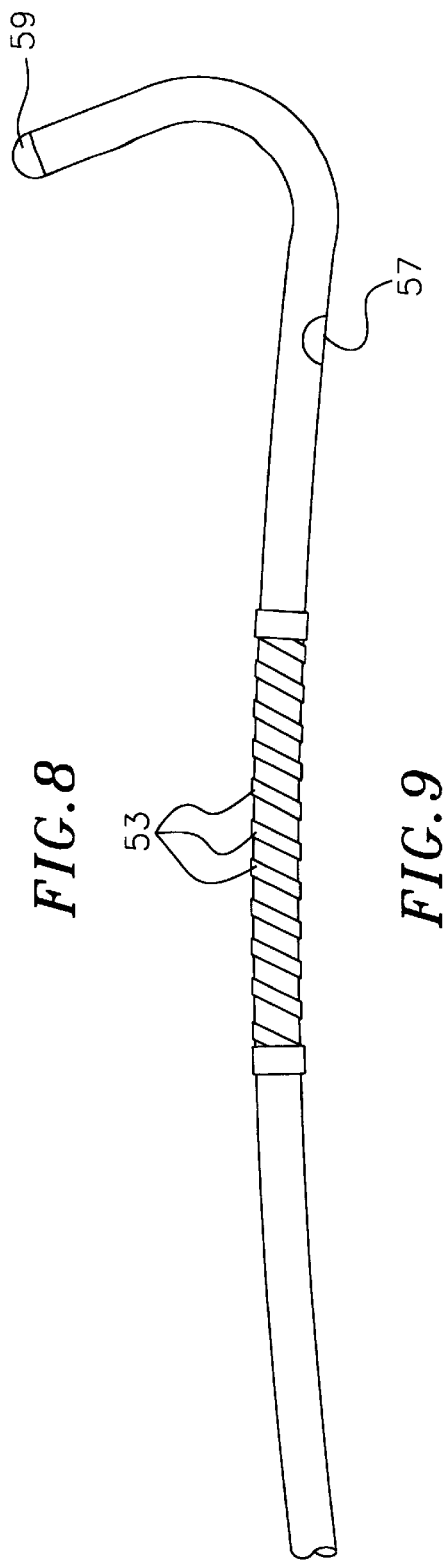
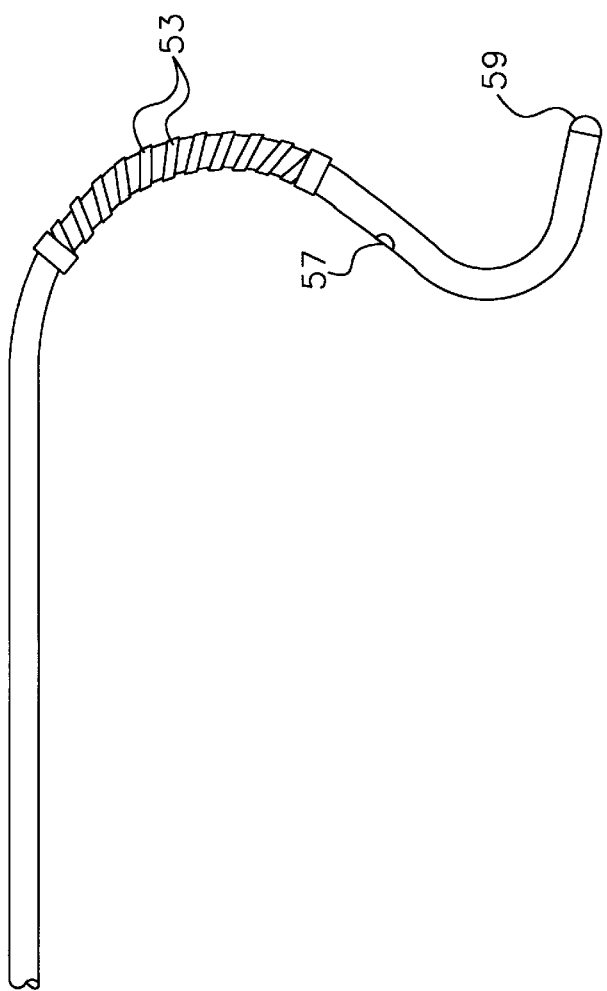
FIG. 8
FIG. 9

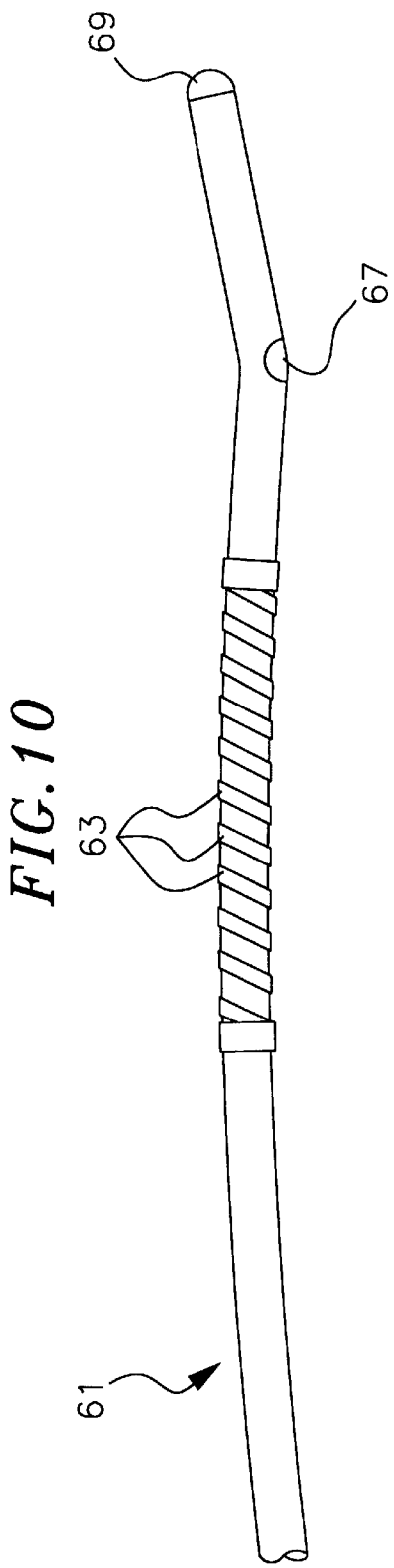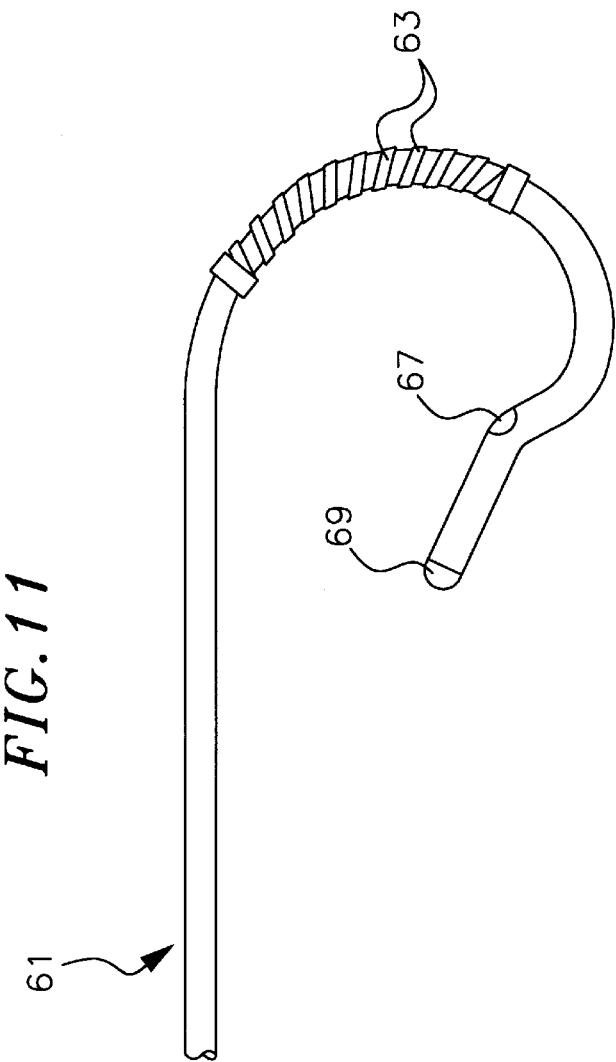

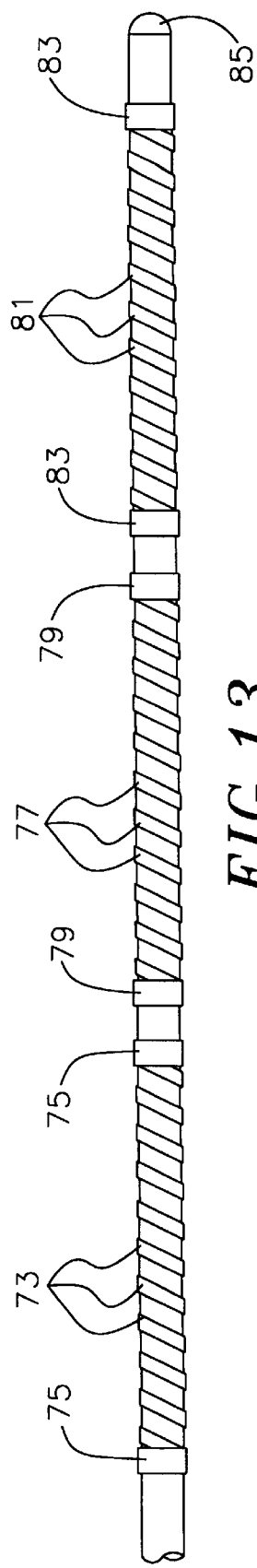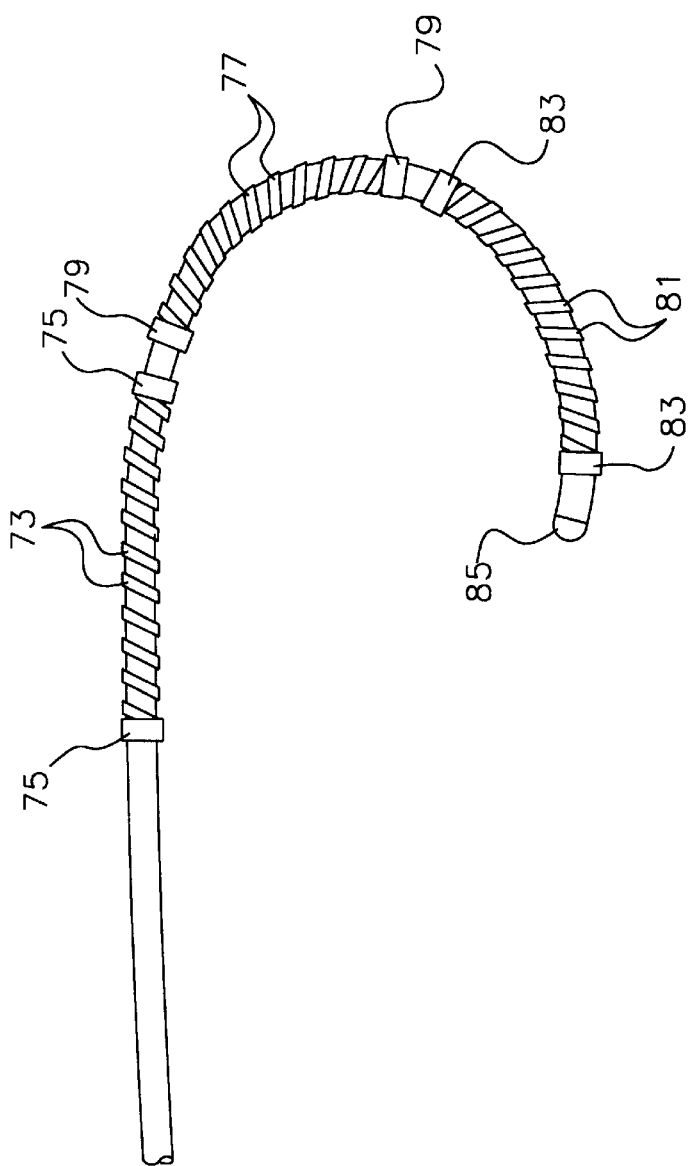
FIG. 12
FIG. 13

CATHETER WITH A SPIRALLY WOUND FLAT RIBBON ELECTRODE

FIELD OF THE INVENTION

The present invention relates to electrode catheters that are useful for creating lesions in and around the heart to disrupt conduction pathways that are causing abnormal heart rhythms. The catheters of the present invention are also useful for monitoring electrophysiologic signals in the heart.

BACKGROUND OF THE INVENTION

Creating lesions in and around the heart by radio frequency (RF) ablation is well known in the art of cardiac electrophysiology. It consists of applying RF energy, usually in the range of about 300–1200 kHz, to the inner surfaces of the heart by an electrode located at the distal section of a catheter. The RF energy generates heat in the heart tissue that is juxtaposed to the electrode. The heat kills the tissue and thereby destroys the electrochemical junctions between the cells and thus blocks the electrical conduction. The dead tissue is eventually replaced with scar tissue which is a very poor conductor of electrical current. Thus, a permanent blockage of a conduction pathway will occur.

RF ablation has worked very well for the treatment of supra ventricular tachycardias. These tachycardias are caused by discrete pathways which are easily pinpointed and destroyed by small focal lesions.

There are, however, other abnormal rhythms which include atrial flutter, atrial fibrillation, and other ventricular tachycardias whose electrical pathways range over broader areas. These abnormalities usually require a number of small lesions forming one or more continuous lines to completely ablate the conduction pathways causing the abnormality.

Unfortunately, a continuous lesion line is often difficult to generate with multiple small lesions. One reason for the difficulty is that the catheter must be guided from a remote entry site, such as the groin, while viewing the electrode on an X-ray monitor. It is very difficult to systematically make a number of small lesions in a continuous line from such a remote site. Another reason for the difficulty is that the heart is beating and constantly changing shape. Creating a continuous linear lesion by making a number of small focal lesions in a beating heart is almost impossible. Finally, difficulty lies in that the interior of the heart is irregularly shaped and covered with trabeculae.

In attempting to overcome these difficulties, some electrophysiologists have tried creating long linear lesions using a long cylindrical rigid electrode. However, the long cylindrical electrode has the problem of lack of flexibility. The problem arises because the distal section of the catheter has to be nearly straight to be introduced into the body and guided through the major blood vessels and into a heart chamber. Once in the heart chamber, the electrode almost always needs to be curved to achieve good contact with the heart tissue to be ablated. Thus, a rigid electrode is not practical.

Others have tried using a long thin strip shaped electrode that extends longitudinally in parallel to the axis of the catheter along the outside of the distal section. To ensure good adhesion to the catheter, the strip electrode needs to be glued or fastened to the catheter all along its entire length. Unfortunately, the glue or adhesive used impairs the flexibility of the distal section. Also, because the interior of the heart is irregularly shaped and covered with trabeculae, it is difficult to achieve good connection with heart tissue using the long thin strip shaped electrode. Many times contact with the catheter and the heart tissue occurs on the side of the catheter where the electrode is not physically located. A final problem with the strip electrode is that when the strip is attached to the catheter's distal section, the stiffness of the strip itself makes the catheter too rigid and the catheter does not bend properly.

Another attempt to create long linear lesions is to use closely spaced apart ring electrodes. If the ring electrodes lie on the catheter surface and are spaced apart just enough to give the tip some flexibility but not interrupt the continuity of the lesion, then the ring electrodes must be securely fastened to the catheter to prevent the electrodes from slipping off the catheter. The glue or adhesive used to fasten the electrodes will greatly diminish the flexibility of the end. On the other hand, if the ring electrodes are flush with the catheter surface and closely spaced apart in order to create a continuous linear lesion, the flexibility of the catheter will also be diminished do to the stiffness of the ring electrodes. Additionally, flush electrodes have problems getting good tissue contact to ablate the close spacing of the flush ring electrodes is such that there is not enough flexible catheter material between each electrode to afford any degree of flexibility. Another drawback with the multiple ring electrodes is that a separate lead wire would have to be attached to each one of the many individual ring electrodes. In catheters with small inner diameters, it is difficult to manufacture the catheters with many lead wires.

Another attempt at creating linear lesions is to use a coil of wire wrapped around the distal section of the catheter body. Unfortunately, this catheter also has many drawbacks. The wire is small in order to keep the catheter diameter small. This small diameter results in a high resistance compared to the interface of the surface of the coil and the tissue. In other words, it results in a circuit where the source resistance is high compared to the load resistance.

Accordingly, there is a need for a catheter that is useful in creating long linear lesions. One important requirement for the linear ablation electrode is that the electrode and distal section of the catheter remain flexible so that the electrode can be passed into a heart chamber and then be made to conform to the irregularly shaped heart surface. Another important requirement is that the electrode be fixed relative to the heart and not move during the ablation process so that providing RF energy to the heart will result in a continuous lesion without breaks.

SUMMARY OF THE INVENTION

The present invention overcomes the above problems and pertains to a catheter with a spirally wound flat ribbon electrode that wraps around the catheter. More specifically, the catheter comprises a tubular body with proximal and distal sections. The distal section comprises a flexible section. The proximal section is provided with a connector. The flexible distal section is covered by a spirally wound flat ribbon electrode made out of a suitable electrically conductive metal. The flat ribbon electrode is tightly wrapped around the distal section in a spiral configuration. The tight spiral wrap ensures that an RF lesion created by the catheter will be continuous linearly. A lead wire is connected to the spirally wound electrode.

The catheter according to the present invention is especially designed to be useful for treating cardiac arrhythmias. For this purpose, the distal section of the catheter with the spirally wound flat ribbon electrode is maneuverable and curves into place tightly against the interior wall of the heart.

RF energy is then supplied to the electrode to heat and kill the surrounding tissue. Consequently, electrical conduction through the ablated tissue of the heart will be interrupted. By this invention, a smaller, longer, more precise area of the heart can be inactivated when compared with ablation catheters of the prior art.

By placing one or more spiral electrodes on a flexible deflectable distal section of a catheter, a long linear lesion can be made without moving the catheter. If several short spiral electrodes are placed closely together so that their ends almost touch, the long linear lesion can be formed one electrode at a time by sequentially supplying RF energy to each spiral electrode. This method of ablation reduces the amount of energy required at any given time which reduces the heat generated by the lead wires and prevents overheating the body of the catheter.

In a further embodiment, polyurethane or latex has been used to mask off a portion of the spiral electrode which contacts the blood leaving exposed the portion of the spiral electrode which contacts the heart tissue. This configuration forms an intermittent strip of the spirally wound flat ribbon electrode which, as previously described, forms a continuous linear ablation lesion. The RF energy loss to the blood is minimized thereby minimizing the RF energy required per unit length of lesion formed. Conversely, the length of lesion formed at any one time is increased, limited only by the maximum allowable energy that is set by lead wire heating within the catheter.

The catheter with a spirally wound flat ribbon electrode is replete with advantages. The spiral configuration allows great flexibility of the distal section of the catheter. Because the electrode wraps around the catheter, it is easier to achieve a good connection with the heart tissue despite its irregular shape and being covered with trabeculae. Only one lead wire needs to be associated with each spiral electrode thereby greatly reducing the number of lead wires traversing through the catheter's body.

A plurality of spirally wound flat ribbon electrodes can be adhered to the distal section of a catheter. The electrodes could be used for ablation or the electrodes could be connected to a monitor to record and map electrophysiologic signals from the heart, or some of the electrodes could be used for ablation while others are simultaneously used for monitoring electrophysiologic signals. The spiral flat ribbon electrode lies atop the catheter surface but because it is one continuous piece of metal with high tensile strength, it requires a minimal amount of glue for placement and stability thereby affording a maximal amount of flexibility.

As will be realized, the invention is capable of other and different embodiments and its several details are capable of modification in various respects, all without departing from the spirit and scope of the present invention. Accordingly, the drawings and detailed description are to be regarded as illustrative in nature and not as restrictive.

BRIEF DESCRIPTION OF THE DRAWINGS

Embodiments of the invention will now be described with reference to the following drawings which:

FIG. 2a is a cross section of the distal section of the catheter of FIG. 1 at line 2a—2a;

FIG. 5a is a longitudinal cross section of a distal section of a catheter according to the invention;

FIG. 5b is a longitudinal cross section of an alternate attachment of a distal section of a catheter according to the invention;

FIG. 8 is a plan view of an alternate embodiment of the invention;

FIG. 9 is a plan view of the embodiment of FIG. 8 when contracted;

FIG. 10 is a plan view of another alternate embodiment of the invention;

FIG. 11 is a plan view of the embodiment of FIG. 10 when contracted;

FIG. 12 is a plan view of an additional embodiment of the invention;

FIG. 13 is a plan view of the embodiment of FIG. 12 when contracted;

DETAILED DESCRIPTION

Figure 1:
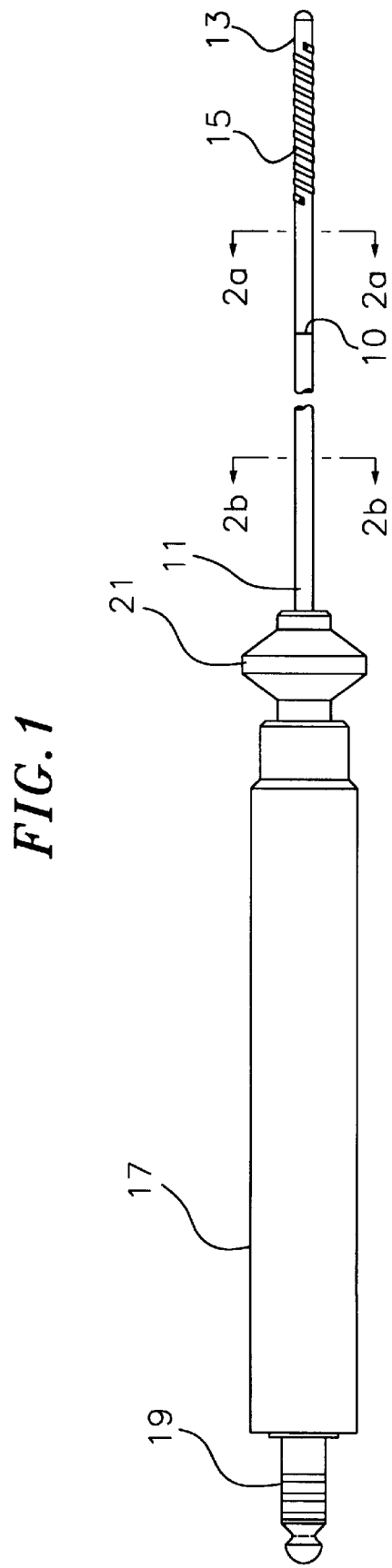
FIG. 1 is a schematic view of a preferred electrode catheter of the present invention.

Turning in detail to the drawings, FIGS. 1, 2a, 2b, 2c and 3 illustrate an electrode catheter constructed in accordance with the present invention. The electrode catheter comprises an elongated tubular catheter body having a proximal section 11 and a distal section 13. Spirally wrapped around the outer surface of the distal section is a flat ribbon electrode 15. A handle 17 is connected to the proximal section of the catheter body 11. Connected to the handle is a connector 19 which is electrically connected to the spiral electrode via a lead wire 25 which traverses through the catheter as described below. RF energy supply (not shown) can then be connected to the connector and thereby connected to the lead wire which is connected to the spiral electrode.

Figure 2A:
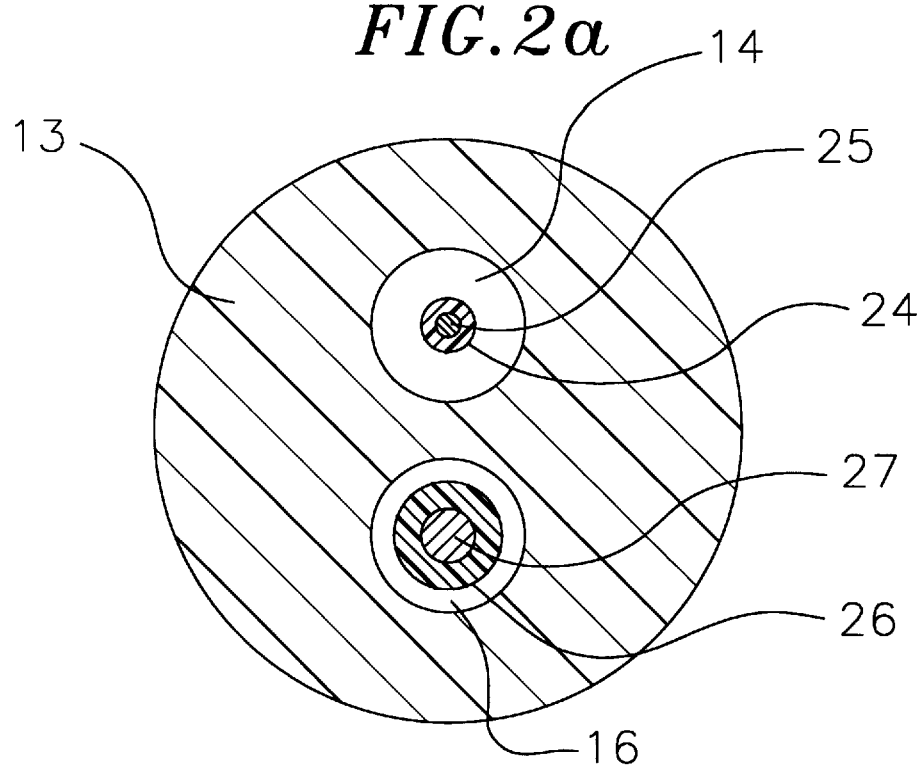
Figure 2B:
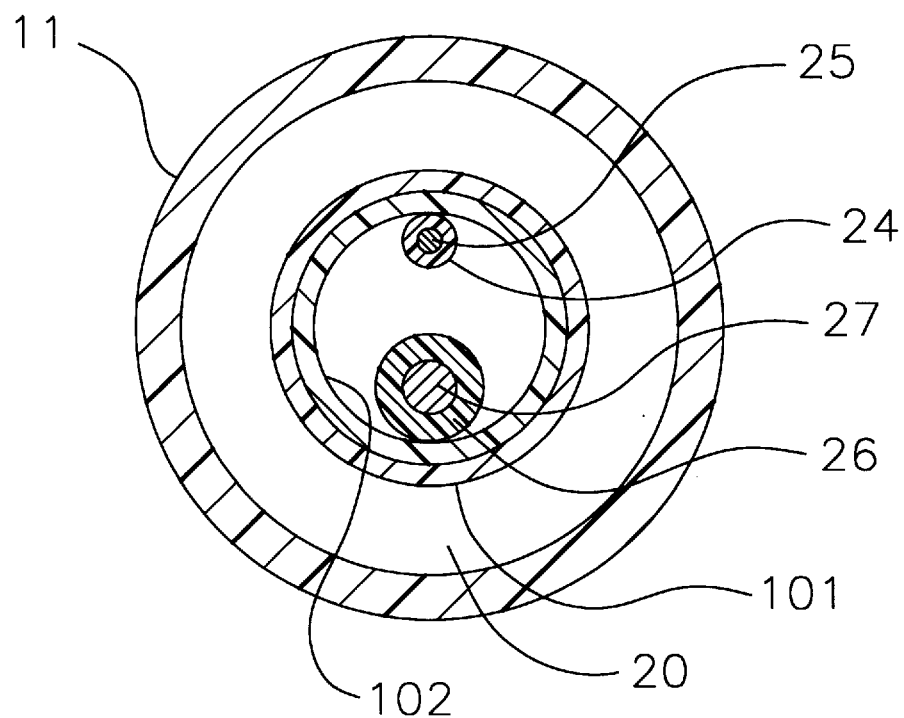
FIG. 2b is a cross section of the catheter body of FIG. 1 at line 2b—2b.
Figure 2C:
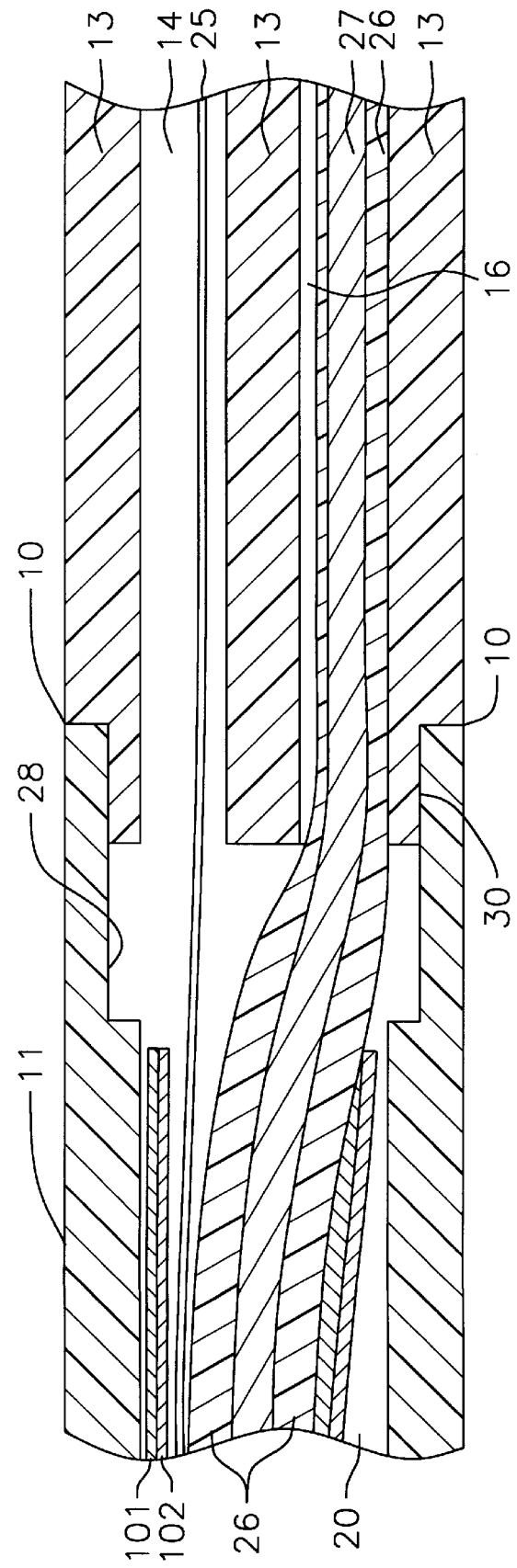
FIG. 2c is a longitudinal cross section of the junction of the proximal section and the distal section.

As best illustrated in FIGS. 2a, 2b and 2c, the proximal section 11 comprises an elongated tubular section having a single proximal lumen 20. The catheter body 11 is flexible, i.e., bendable, but substantially non-compressible along its length. The body of the catheter at the proximal section 11 may be of any suitable construction and made of any suitable material. At present, preferred construction comprises a nylon tube surrounded by braided stainless steel sandwiched within polyurethane. The length and diameter of the catheter body 11 are not critical. For the electrode catheter shown in the accompanying drawings, a length of about 40–48 inches, an outer diameter of about 0.1 inch or 8 French, and an inner diameter, i.e., lumen diameter, of about 0.03–0.04 inches is presently preferred.

The distal section 13 is shorter in length than the proximal section. Depending on the embodiment used, the length of the distal section will also vary. Currently a range from about one inch to about eight inches is preferred. The distal section is made out of flexible tubing having dual non-overlapping, e.g. side by side, first and second distal lumens 14 and 16 which are off axis, i.e., not coaxial with the distal section 13. The tubular cylindrical wall of the distal section 13 may be made of any suitable material and is more compressible and preferably, more flexible, i.e., bendable, than the catheter body 11. A presently preferred construction for the distal section portion 13 comprises a thermoplastic resin, e.g., polyurethane, optionally reinforced with a stainless steel braid. The diameter of the distal section 13 is not critical, but it is preferably about the same as or slightly smaller than the diameter of the catheter body 11. The hardness at the section should be a Shore hardness of 55 D or less.

A preferred means for attaching the distal section 13 to the proximal section 11 is shown in FIG. 2c. The joining end of the distal section 13 comprises an outer circumferential step 30 and the joining end of the proximal section 11 comprises an inner circumferential step 28. The steps 28 and 30 are sized to allow the joining end of the distal section 13 to be snugly inserted into the joining end of the proximal section 11. The proximal section 11 is then fixedly attached to the distal section 13 by glue, or the like, to form seam 10. As shown, the proximal lumen 20 of the proximal section is in communication with both off-axis distal lumens 14 and 16 of the distal section.

Figure 3:
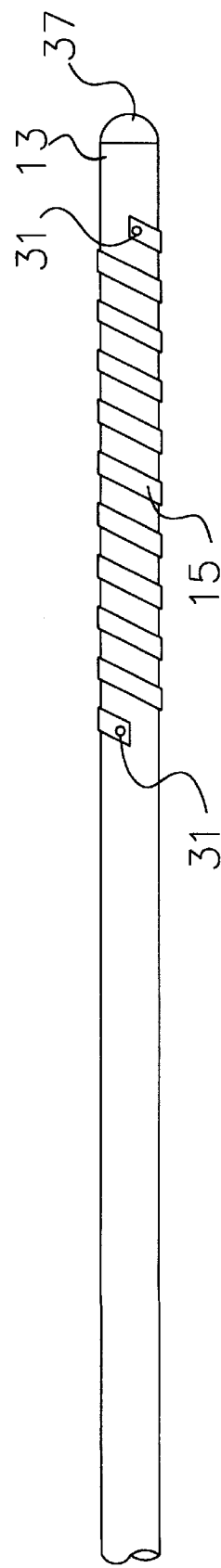
FIG. 3 is a plan view of the distal section of the catheter of FIG. 1.

At the distal section 13 of the catheter is a spiral flat ribbon electrode 15. The spiral electrode has proximal and distal ends. As can be seen by FIG. 3, the proximal and distal ends are attached to the outer circumference of the flexible distal section 13 of the catheter. The fixation of the ends could be by pins 31 that act as rivets fastening the ends of the spiral electrode to the catheter wall. In another embodiment illustrated in FIG. 4, the ends are attached by circular rings 32. The circular rings are glued all around the outer surface of the distal section of the catheter and anchor the ends of the spiral electrode to the catheter. The spiral flat ribbon electrode lies on top of the catheter surface, but because it is one continuous piece, it requires a minimum amount of fixation to retain the electrode on the catheter and thereby affording the maximum amount of flexibility. By lying on top of the surface, the flat ribbon electrode can exhibit pressure on the tissue to maximize the ablation process. Further, by being a flat ribbon, it maximizes the cross sectional area and minimizes the length of the flat ribbon spiral which minimizes its electrical resistance in order to deliver uniform RF energy over the length of the spiral to the tissue.

The spirally wound flat ribbon electrode is made out of any suitable electrically conducting metal. Preferably the metal is platinum or an alloy of platinum and iridium. In a preferred embodiment, the electrode is cut from a flat piece of metal with a thickness of approximately 0.002–0.003 inches. The width of the ribbon can very, but preferably should be about 0.025–0.030 inches. In the alternative, the electrode is laser cut from a cylindrical metal tube with a diameter corresponding to the diameter of the distal section. If the ribbon is cut from a flat piece of metal, the ribbon should be cut long enough to be wrapped around the catheter body. If the ribbon is laser cut from a metal tube with the proper diameter, then the ribbon can be cut to the exact desired length for placement onto the catheter. In the preferred embodiment, the flat ribbon electrode is tightly wrapped in a spiral configuration at a rate of about seven wraps per centimeter. This tight wrap ensures that a lesion formed by using RF energy will overlap in the space between the wrappings. Thus, a continuous linear lesion is formed.

Once the electrode has been cut and properly shaped, it is ready to be slid over the distal section 13 of the catheter. As illustrated in FIG. 5, the distal section 13 has two distal lumens 14 and 16 with an electrical lead wire 25 extending through the distal lumen 14. The insulation 24 of the electrical lead wire is stripped off at its distal end. The lead wire extends through a small hole 23 in the wall of the catheter and is in electrical connection with the spiral electrode 15 by welding or soldering the lead wire to the electrode.

In constructing the catheter, it is preferred to first thread the electronic lead wire through the hole in the catheter wall. The end of the spiral electrode can then be soldered to the electrical lead wire. Then the whole spiral electrode can be slid over the end of the catheter until it is in the correct location. Once the electrode is in place, slack on the electronic lead wire can be pulled taut.

Figure 4:
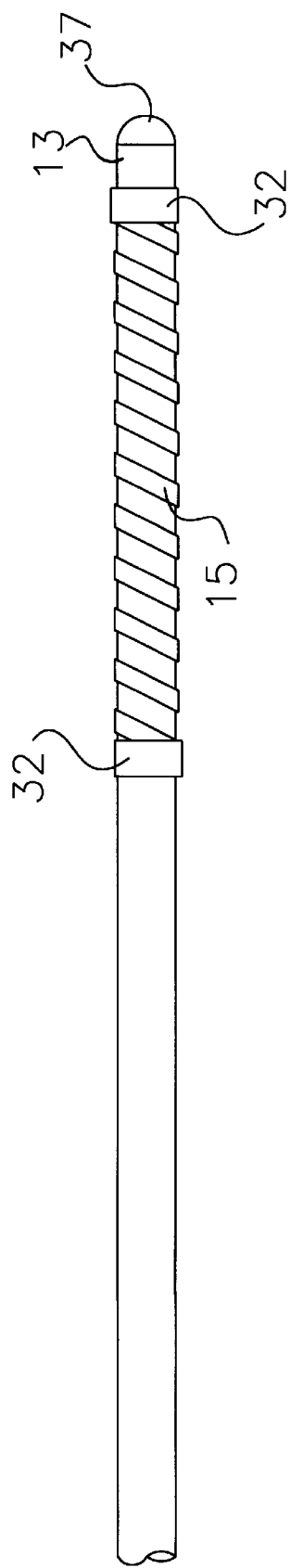
FIG. 4 is a plan view of an alternate embodiment of a distal section of a catheter.
Figure 6:
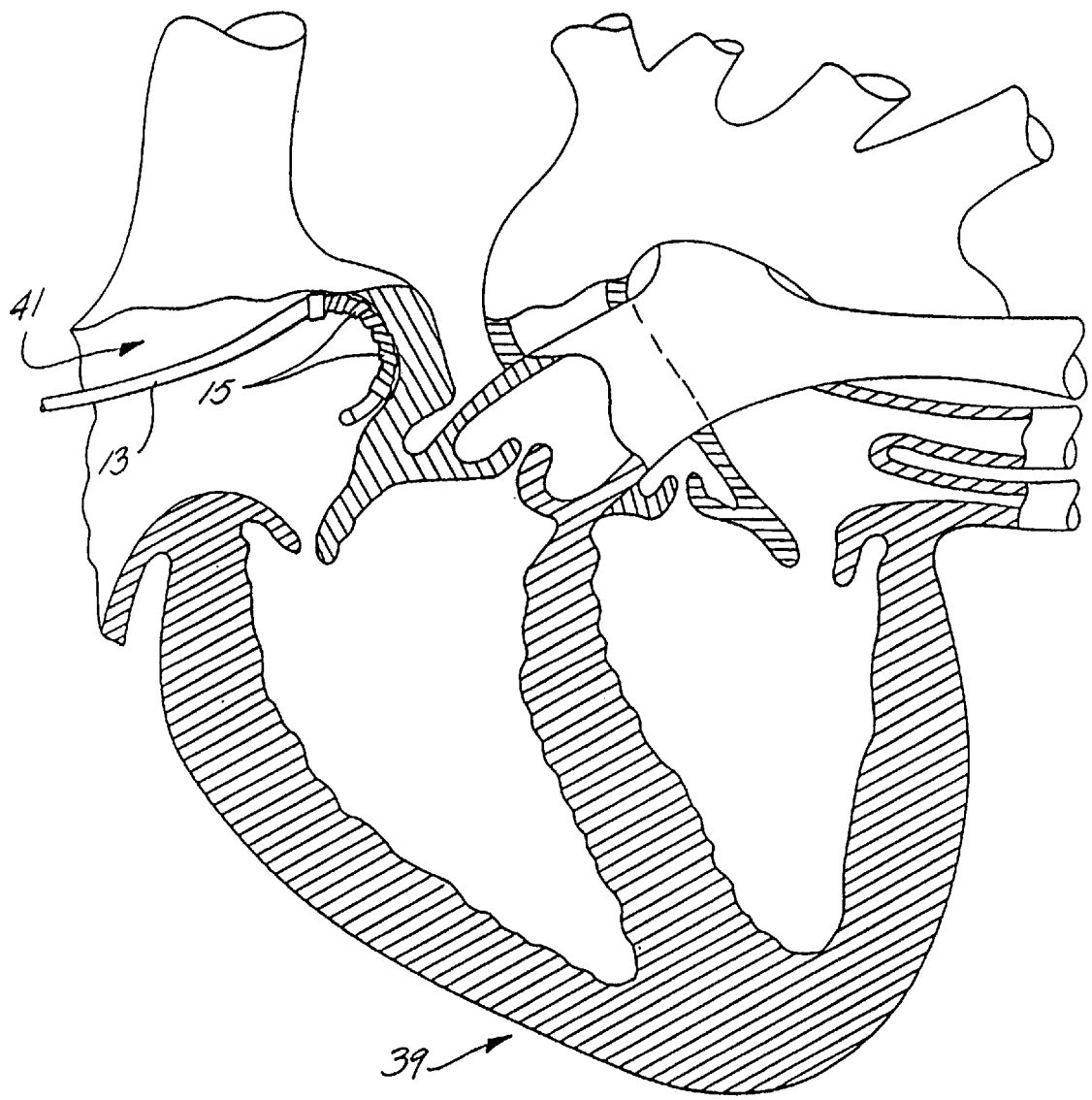
FIG. 6 illustrates an application of the invention in the right atrium.
Figure 7:
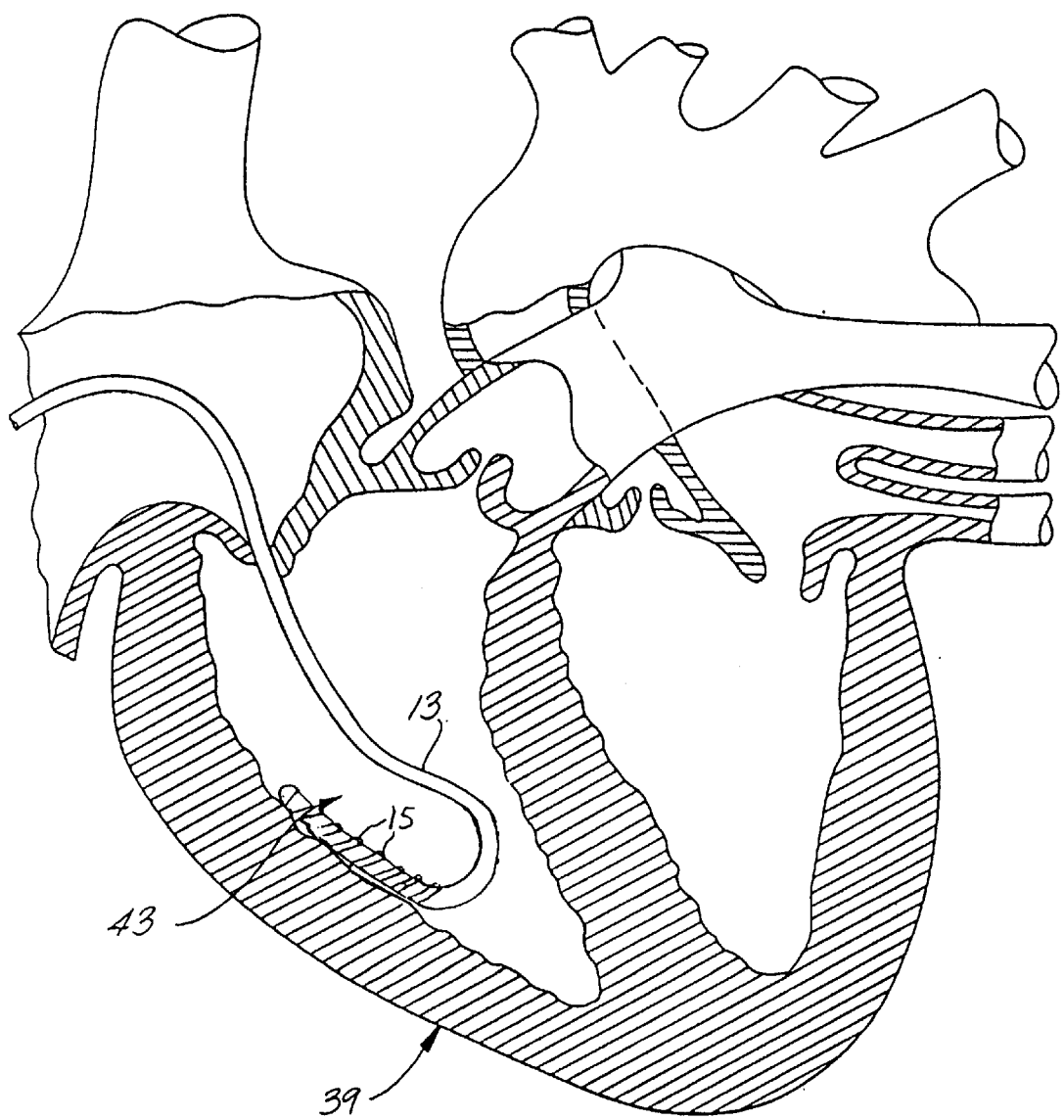
FIG. 7 illustrates an application of the invention in the right ventricle.

When the spiral electrode is in the correct position on the distal section, the free ends of the spiral electrode are secured. This can be done by at least two different ways. First, as illustrated in FIG. 3, the ends can be fastened to the distal section with pins 31 which act as rivets fastening the ends to the distal section. Secondly and currently the preferred method, as illustrated in FIG. 4, the ends of the spiral electrode are fastened to the distal section by rings 32 clamped and glued around the catheter.

Depending on the length of the spiral electrode, the spiral electrode may need to be secured at other areas along its length. If the electrode needs to be secured, the electrode is glued at discrete areas along its length to the distal section. The glue should be used sparingly, however, in order to not interfere with the flexibility of the distal section. In the preferred embodiments, when the body of the spiral electrode is glued, it is only glued along one longitudinal axis of the distal section 13. In this way, the remaining axes are free to move in relation to the distal section and flexibility is maintained.

The distal section remains highly flexible when the spiral flat ribbon electrode is attached. It is believed that the flexibility is maintained for several reasons. First, because the electrode is made out of a flat ribbon of metal, the tensile strength is strong enough that only a minimum of glue is needed to adhere the electrode to the distal section. The less glue that is used, the greater the distal section's flexibility. Secondly, due to the spiral wrapping, it is believed that when the distal section flexes it also twists. The twisting motion allows the distal section to bend easier.

The catheter is preferably steerable by use of a puller wire 27. The puller wire 27 is preferably made of stainless steel or NITINOL. The puller wire extends from the control handle 17 through the proximal lumen 20 of the proximal section 11 of the catheter and into the distal section 13 through distal lumen 16. As illustrated in FIG. 2b, the puller wire is encircled by a teflon sheath 26, or the like, for lubricity and to keep the puller wire generally coaxial in the proximal section. For additional coaxial strength, the puller wire is optionally placed in a nylon tube 101 that has an inner polyimide tube 102 glued within the nylon tube. As illustrated, the lumen of the nylon/polyimide tube is large enough to accommodate the puller wire 27 and the lead wire 25. At the junction 10 of the proximal section with the distal section, the nylon/polyimide tube has a free distal end. The puller wire extends out of this free distal end and into distal lumen 16 of the distal section 13 of the catheter. In the distal lumen 16, the teflon sheath 26 is swaged, i.e., thinned to smaller wall thickness to accommodate the smaller distal lumen 16 of the distal section 13.

In the embodiment shown in FIG. 5a, the puller wire 27 extends through the distal lumen 16 of the distal section and is fixedly attached to the distal tip 37 of the catheter. A preferred means for attaching the puller wire 27 is described in U.S. Pat. No. 4,960,134 and U.S. Pat. No. Re 54,502 which are incorporated herein by reference. An anchor 33 is fixably attached, e.g., crimped, to the distal end of the puller wire 27. The anchor 33 is then wedged against the free end of the distal section 13 of the catheter and secured by glue, or the like. The exposed edges of the anchor 33 is preferably covered with a suitable resin material 37, or the like, to form a smooth rounded distal tip.

In an alternate embodiment, the puller wire is secured to the distal section 13 of the catheter along its wall. A preferred means for attaching the puller wire 27 to the wall of the distal section is shown in FIG. 5b and comprises a short piece of tubular stainless steel 29, e.g., hypodermic stock, which is fitted over the distal end of the puller wire 27 and crimped to fixedly secure the puller wire. The distal end of the tubular stainless steel crosspiece is fixedly attached, e.g. by welding, to a stainless steel crosspiece 36 which fits into a notch 34 in the wall of the flexible tubing of the distal section 13 of the catheter which extends into the distal lumen 16. The crosspiece is larger than the distal lumen and therefore cannot be pulled into the distal lumen. The portion of the notch not occupied by the crosspiece is filled with glue, or the like, preferably a polyurethane glue harder than the material of the flexible tubing. Any rough edges are polished off to provide a smooth outer surface.

The off-axis distal lumen 16 that the puller wire travels through allows for consistent curvature of the distal section 13 by controlling the longitudinal movement of the puller wire. Because the proximal lumen 20 of the proximal section 11 is coaxial with the catheter body, the puller wire does not exert force on the proximal section 11. However, because the puller wire is offset from the axis at the distal section 13, the distal section 13 bends in the direction of the offset, as illustrated in FIGS. 9, 11, 13 and 16 when the puller wire is pulled proximally relative to the distal section 13.

Any suitable control handle 17 which can control longitudinal movement of the puller wire 27 relative to the catheter body may be used. A preferred control handle 17, as shown in FIG. 1, is described in U.S. Pat. No. 4,960,134 and Re U.S. Pat. No. 34,502 which are incorporated herein by reference. The handle has a thumb rest 21 that controls the longitudinal movement of the puller wire. Movement of the puller wire longitudinally relative to the catheter body 11 will control the curvature of the distal section 13. Proximal movement of the puller wire with respect to the catheter body will cause the distal section 13 to become curved. Distal movement of the puller wire with respect to the catheter body will allow the catheter to extend back to its resting shape.

Some embodiments illustrate the distal end of the puller wire 27 connected to the side of the distal section 13 of the catheter. FIGS. 8 and 9 illustrate a catheter that has a preformed curve proximate to the distal tip 59 and distal to the puller wire attachment at notch 57. The preformed curve may be useful for positioning the distal section of the catheter in certain anatomical regions of the heart. The hole 57 is cut into the side of the distal section 13. The puller wire, anchor, and cross section are then wedged into the notch as described above. The notch is then sealed with an appropriate glue or resin material. By fastening the puller wire to the side of the catheter, proximal longitudinal movement of the puller wire will result in the catheter bending and exposing the spiral electrode 53 as illustrated in FIG. 9. The preformed curved portion of the distal section, however, does not bend when the puller wire is moved. The same principle is illustrated in FIGS. 10 and 11 where the puller wire is anchored to notch 67. The distal section 61 has a preformed bend proximate to the distal tip 69. Proximal longitudinal movement of the puller wire will result in the distal section bending to expose the spiral electrode 63 without bending at the preformed bend.

FIGS. 12 and 13 illustrate another embodiment of the present invention. In this embodiment, three spiral flat ribbon electrodes 73, 77 and 81 are illustrated. Spiral electrode 73 is anchored to the distal section by rings 75, spiral electrode 77 is anchored to the distal section by rings 79, and spiral electrode 81 is anchored to the distal section by rings 83. The spiral wrap of each electrode is in the same direction. Thus, when the puller wire attached to the distal tip 85 is pulled in a longitudinal direction proximally, the catheter will bend and twist slightly due to the spiral wrapping.

Figure 14:
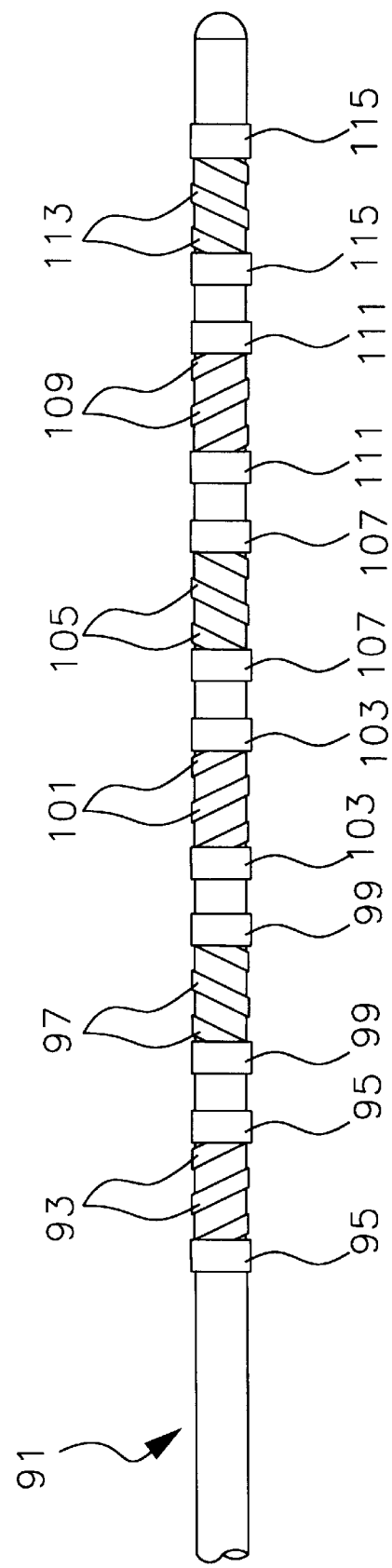
FIG. 14 is a plan view of a distal section of a catheter of the invention with a plurality of spiral electrodes wound in opposite directions.

Another embodiment is illustrated in FIG. 14. Six small spiral flat electrodes are adhered to the distal section 91. The wrapping of the spiral electrodes are alternated, with electrodes 93, 101 and 109 wrapped in the same direction and electrodes 97, 105 and 113 wrapped in the opposite direction. Each electrode is adhered to the catheter with corresponding rings 95, 99, 103, 107, 111 and 115. Because the wrapping of each spiral electrode alternates, any twisting of the catheter when the catheter is flexed will neutralize out and the distal section will bend in a straight curve.

The length of each spiral electrode in the embodiment illustrated in FIG. 14 is kept relatively short, approximately two centimeters. The short length facilitates the use of the catheter as a mapping catheter as well as an ablation catheter. For use in mapping, a separate lead wire is connected to each individual spiral electrode. The lead wire is also connected by means of a connector to an electrophysiologic monitor.

Figure 15:
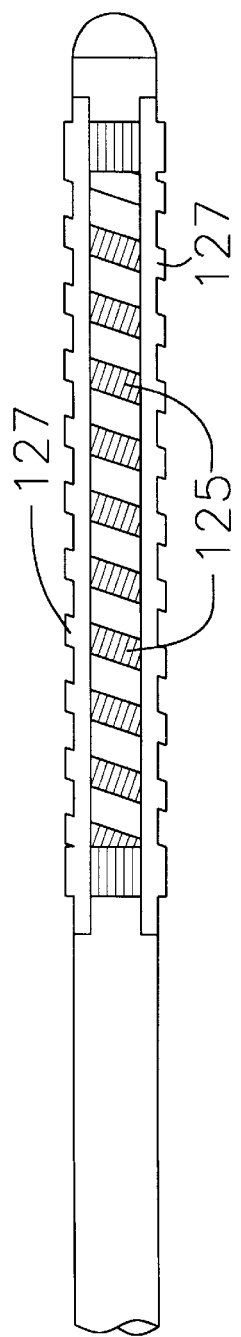
FIG. 15 is a plan view of a further embodiment where the spiral electrode has been partially masked off.
Figure 16:
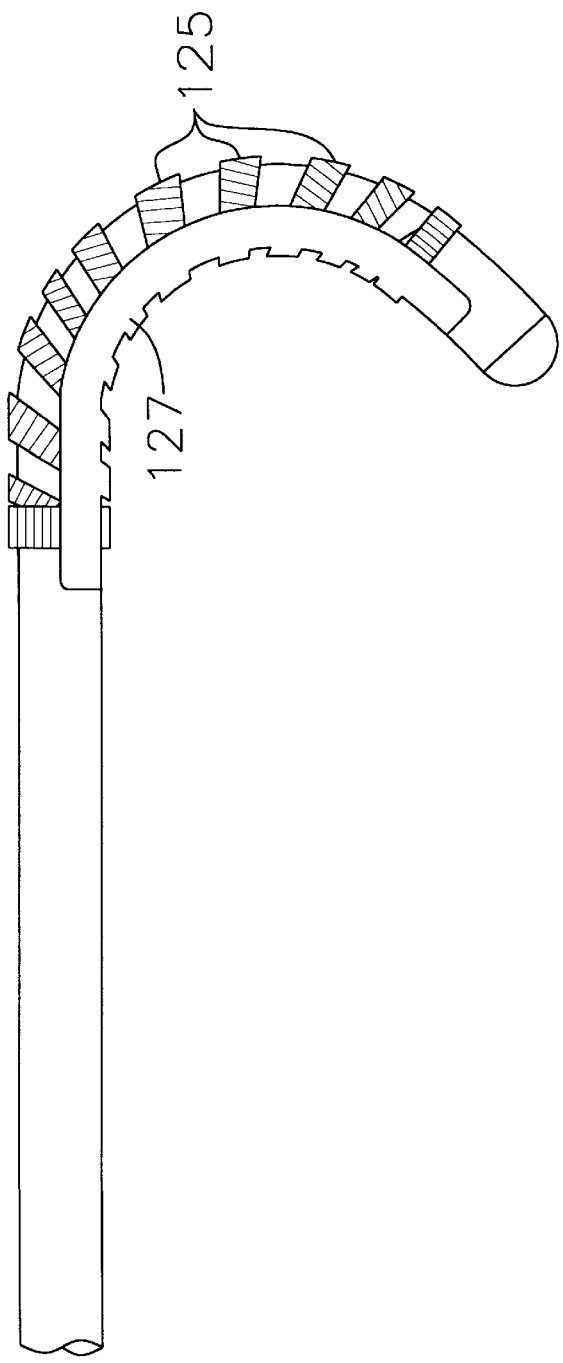
FIG. 16 is a plan view of the embodiment of FIG. 15 when contracted.

In a further embodiment as illustrated in FIGS. 15 and 16, a portion of the spiral electrode 125 has been masked off with mask 127. The portion masked off is the portion of the spiral electrode which would contact the blood pool instead of heart tissue. This is the concave surface of the catheter when it forms a curved shape by use of the puller wire. The convex portion that would contact heart tissue has been left exposed. This configuration forms an intermittent straight strip electrode which forms a continuous linear lesion due to the tight wrapping of the spiral electrode. By masking off the portion of the spiral electrode in contact with the blood pool, the energy loss to the blood pool is minimized thereby minimizing the energy required per unit length of lesion formed. Conversely, the length of the lesion formed at any one time is increased, limited by the maximum allowable energy that is set by lead wire heating within the catheter body.

The mask 127 can be a wide variety of materials that can be applied over the spiral after it is assembled onto the section and which has the following properties:

1. Can be applied in a thin flexible coating to leave a well defined strip uncoated by brushing, spraying, dipping or some other practicable process.
2. Has good electrical insulating properties.
3. Has good thermal conductivity.
4. Has good adhesion for 12 hours in the vascular system.
5. Has good biological properties such as hydrolytic stability and biocompatibility for a 12 hour catheterization.

The presently preferred material for masking is a polyurethane. One such polyurethane is supplied by E. V. Roberts, Culver City, Calif., called System RF-1737. This material has a high viscosity and a very short pot life. The polyurethane system is modified before mixing the two parts together by adding sufficient solvent to delay its setting up and lowering its viscosity considerably. The preferred solvent used is two parts tetrahydrofuran (supplied by numerous manufacturers, Aldrich Chemical Company, Inc., Milwaukee Wis., being one) and one part p-Dioxane (also supplied by numerous manufacturers, E.M. Science, Gibbstown, N.J., being one). The resulting solution (paint) can then be painted onto the desired area of the distal section and spiral electrode by using a fine artist's paint brush. The painted surface is tack free within one hour and cures fully after 2 hours at 100° C.

Alternatively, the spiral masking 127 can be obtained by dipping the distal section in a latex solution and completely coating it with a very thin coating of a elastomer such as a polyurethane latex with a shore hardness of 50 D or less. The latex is then fully cured by heating in a dry oven and then "sandblasted" with a well defined jet of sodium bicarbonate. The jet of sodium bicarbonate removes the latex mask where desired with high resolution leaving the metal spiral undamaged.

In practice, the catheter according to the present invention can be used to treat numerous cardiac arrhythmias. For right sided procedures, the catheter is usually introduced into the femoral vein in the groin and advanced into the right atrium 41 of the heart 39 of the patient. By careful manipulation of the catheter, the spiral electrode will be placed firmly against the inner wall of the right atrium. Because the distal section and the spiral electrode are flexible, the spiral electrode can be maneuvered over its entire length against the atrial wall for achieving a precisely desired positioning.

The area surrounding the distal section 13 of the catheter can be made visible in the usual manner in a catheterization laboratory by using X-rays. Thus, by visual inspection of an X-ray monitor, the position of the catheter can be confirmed.

As soon as the spiral electrode is positioned correctly, RF energy is applied, and as a result heart tissue surrounding the spiral electrode will heat and be ablated. Due to this tissue ablation, a conduction block is created, terminating a cardiac arrhythmia. The catheter can also be manipulated in such a fashion that the spiral electrode can be positioned against the atrial wall in several places to effect the required superficial disturbance of the tissue. Also, many spiral electrodes, while narrow in width, may be connected in series to any desired length to produce treatment along a desired line.

Typically, for the treatment of atrial flutter, the conduction pathways are located in the right atrium and ablation is usually needed in the areas of the coronary sinus os, the tricuspid annulus, and the inferior vena cava. For treatment of atrial fibrillation, long linear continuous lesions are usually needed in the right atrium. Occasionally, the left atrium also has to be ablated by using a transeptal approach.

Treatment for ventricular tachycardias requires ablation in the left or right ventricle. Access to the right ventricle is through a right sided approach. The catheter is introduced into the heart described above and advanced into the right ventricle 43. The catheter is then curved and manipulated such that it rests in the desired area of the right ventricular wall. RF energy is then be applied to the spiral electrode to ablate tissue in the right ventricular wall that was responsible for the ventricular tachycardia.

In a left sided approach, the distal section of the catheter is introduced typically through the femoral artery in the groin, up through the iliac artery into the aorta, and then into the left ventricle through the aortic valve. The spiral electrode is then positioned at the site to be ablated and RF energy is then applied to create the lesion.

The catheter of the present invention can also be used to create a long continuous linear lesion sequentially with the use of multiple spiral electrodes. Referring to FIG. 14, a catheter with multiple spiral electrodes 93, 97, 101, 105 and 113 is introduced into the heart chamber to be ablated. The outside surface of the spiral electrodes could be partially masked as described above to have only the portion of the spiral electrodes coming into contact with the heart tissue exposed. The catheter can then be positioned to ablate the treatment site. The ablation could proceed simultaneously by delivering RF energy to each spiral electrode at the same time. This however, has the disadvantage of generating a large amount of heat in the lead wires within the catheter and could damage the catheter during the ablation procedure.

Alternatively, and preferably, the ablation could proceed sequentially. To perform sequential ablation, RF energy is delivered to the first spiral electrode for a sufficient time to generate a lesion. Then the RF energy is delivered to the next electrode to generate a lesion. The sequential ablation proceeds until all of the electrodes juxtaposed to tissue to be ablated have delivered RF energy to the tissue. Using FIG. 14 as illustrative, RF energy could first be delivered to spiral electrode 113. Then the RF energy is delivered to spiral electrode 109. Then the RF energy is delivered to spiral electrode 105, and so on, until the ablation is completed. This strategy is preferred in that the heat generated by each lead wire is not compounded by having all the lead wires generate heat at the same time. Heat can be dissipated throughout the catheter during the sequential ablation and thus, there is a substantial decrease in the possibility of damaging the catheter during the ablation session.

In using the catheter for mapping electrical activity of the heart, a catheter with a plurality of spiral electrodes is used. The distal section is introduced into the appropriate heart chamber and manipulated such that the electrodes are in contact with the area of the heart to be mapped. Lead wires connected to the spiral electrode are also connected to a recording system to produce electrophysiologic signals for monitoring.

The preferred embodiments have been detailed above. However, other embodiments are possible and advantageous for different uses. For example, it is evident that any number of spiral electrodes can be placed along the section portion in various arrangements. It is also evident that some of the electrodes can be connected to a supply of RF energy for ablation while other electrodes alternatively can be connected to a recording system to produce electrophysiologic signals for diagnosis. The different embodiments may be masked as described above. The shape of the catheter can vary and the catheter can be straight of have differing preformed curves, depending on the area of the heart to be ablated.

Thus, a catheter with a spirally wound flat ribbon electrode is disclosed which is useful in creating linear lesions in the heart and also useful in mapping electrophysiologic signals. While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. A catheter for delivering RF energy to the heart for creating linear lesions in the heart comprising a catheter body with a proximal section and a deflectable, generally linear distal section, the distal section comprising a spirally wound flat ribbon electrode having a plurality of turns, each turn being spaced apart from adjacent turns, each end of the spirally wound flat electrode being fixedly attached to the distal section by a ring.

2. A catheter for delivering RF energy to the heart for creating linear lesions in the heart comprising a tubular body having a proximal section and a generally linear, deflectable distal section, the proximal section having a connector at its proximal end, the distal section having a cylindrical wall with an outer circumference and a flat ribbon electrode spirally wound around the outer circumference of the cylindrical wall, each end of the spirally wound flat electrode being fixedly attached to the distal section by a ring, and wherein the catheter further comprises an electrode lead wire extending from the connector to the spirally wound electrode.

3. The catheter as claimed in claim 2 wherein the spirally wound ribbon electrode has a ribbon thickness of about 0.002 to 0.003 inches, a ribbon width of about 0.025 to 0.030 inches, and is wrapped around the catheter distal section at a rate of about 7 wraps per centimeter.

4. The catheter as claimed in claim 2 further comprising a puller wire having proximal and distal ends extending through the tubular body, the distal end of the puller wire being fixedly attached to the distal section of the catheter, and further comprising a handle connected to the proximal section of the catheter body and the puller wire, wherein manipulation of the handle moves the puller wire longitudinally relative to the catheter body to thereby control the deflection of the distal section of the catheter.

5. The catheter as claimed in claim 4 further comprising a central lumen in the proximal section and an off-axis lumen in the distal section wherein the puller wire extends through the central lumen and into the off-axis lumen.

6. The catheter as claimed in claim 2 the distal section further comprises a plurality of the spirally wound electrodes each with a corresponding electrode lead wire connected to such electrode and the connector.

7. The catheter as claimed in claim 6 wherein some of the spirally wound electrodes are wound in one direction around the outer circumference of the distal section of the catheter and the other spirally wound electrodes are wound in the opposite direction around the outer circumference of the distal section of the catheter.

8. The catheter as claimed in claim 2 wherein the spirally wound electrode is masked along a portion of its outer surface with a mask.

9. The catheter as claimed in claim 8 wherein the mask comprises one of the group of polyurethane or latex.

10. A catheter for delivering RF energy to the heart for creating linear lesions in the heart comprising:

(a) a tubular body having a distal section and a proximal section; wherein the distal section comprises a flexible tubular portion with an outer surface;

(b) a flat ribbon electrode spirally wound around the outer surface of the distal section, each end of the spirally wound flat electrode being fixedly attached to the distal section by a ring;

(c) a connector attached to the proximal section of the tubular body;

(d) an electrode lead wire in electrical connection with the electrode and extending through the tubular body and electrically connected to the connector;

(e) a handle connected to the proximal section of the tubular body;

(f) a puller wire having distal and proximal ends extending through the tubular body fixedly attached at its distal end to the distal section and at its proximal end to the handle; and (g) means for moving the puller wire in a longitudinal direction relative to the proximal section of the tubular body to thereby deflect the distal section.

11. The catheter as claimed in claim 10 wherein the flat ribbon electrode has a thickness of about 0.002 to 0.003 inches, a width of about 0.025 to 0.30 inches, and is wrapped around the outer surface at a rate of about seven wraps per centimeter.

12. The catheter as claimed in claim 11 wherein the spirally wound flat ribbon electrode comprises an outer surface and further comprising a mask covering a portion of the outer surface of the spirally wound flat ribbon electrode.

13. The catheter as claimed in claim 12 wherein the distal section can form a curve with a convex and concave side by use of the puller wire and the mask is located on the side of the catheter that becomes concave.

* * * * *